United States Patent
Horvath et al.

(10) Patent No.: US 6,355,651 B1
(45) Date of Patent: *Mar. 12, 2002

(54) CERTAIN PYRROLOPYRIDINE DERIVATIVES; NOVEL CRF1 SPECIFIC LIGANDS

(75) Inventors: Raymond F. Horvath, North Branford; Alan Hutchison, Madison, both of CT (US)

(73) Assignee: Neurogen Corporation, Branford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/657,634

(22) Filed: Sep. 6, 2000

Related U.S. Application Data

(63) Continuation of application No. 09/368,541, filed on Aug. 5, 1999, now Pat. No. 6,133,282, which is a continuation of application No. 08/542,854, filed on Oct. 13, 1995, now Pat. No. 5,955,613.

(51) Int. Cl.⁷ ............... A61K 31/437; C07D 471/04; C07D 471/14; A61P 25/24
(52) U.S. Cl. ............ 514/292; 514/183; 514/212.05; 514/293; 544/328; 544/331; 544/333; 540/479; 540/583; 546/82; 546/87; 546/113
(58) Field of Search .................. 546/82, 87, 113; 544/328, 331, 333; 540/479, 583; 574/292, 293, 183, 212.05

(56) References Cited

U.S. PATENT DOCUMENTS

| 4,605,642 A | | 8/1986 | River et al. |
|---|---|---|---|
| 5,063,245 A | | 11/1991 | Abreu et al. |
| 5,644,057 A | | 7/1997 | Yuan et al. |
| 6,107,301 A | * | 8/2000 | Aldrich ............... 514/258 |
| 6,133,282 A | | 10/2000 | Horvath et al. |

FOREIGN PATENT DOCUMENTS

| EP | 0 061 056 | 9/1982 |
|---|---|---|
| WO | WO 94/13676 | 6/1994 |
| WO | WO 95/33750 | 12/1995 |
| WO | WO 96/35689 | 11/1996 |

OTHER PUBLICATIONS

Owens et al., (1991), "Physiology and Pharmacology of Corticotropin–releasing Factor", *Pharm. Rev.*, vol. 43, No. 4 pp. 425–473.

Montgomery et al., (1972), "The Use of Enamines in the Synthesis of Heterocycles," *J. Het. Chem.*, vol. 9, pp. 1077–1079.

Zimmerman et al. "Pyrrolo[2,3–b]pyridines" *Arch. Pharm.* vol. 309, pp. 597–600.

* cited by examiner

*Primary Examiner*—Evelyn Mei Huang
(74) *Attorney, Agent, or Firm*—McDonnell Boehnen Hulbert & Berghoff

(57) ABSTRACT

Disclosed are compounds of the formula:

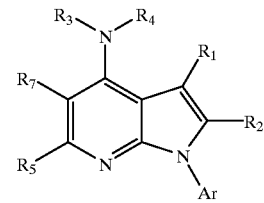

wherein

Ar is optionally substituted aryl or heteroaryl $R_1$ is hydrogen or alkyl;

$R_7$ is hydrogen or alkyl;

$R_2$ is hydrogen, halogen, alkyl or alkoxy; or $R_1$ and $R_2$ taken together with the ring to which they are attached form a 5–9 membered saturated or aromatic ring optionally having a hetero atom selected from oxygen, sulfur or nitrogen;

$R_3$ and $R_4$ are independently hydrogen, alkyl, cycloalkyl, aryl or heteroaryl groups; or $R_3$ and $R_4$ together with the nitrogen atom to which they are attached form a 5–8 membered ring; and $R_5$ is hydrogen, halogen, straight or branched chain lower alkyl having 1–6 carbon atoms, or straight or branched chain lower alkoxy or thioalkoxy having 1–6 carbon atoms, which compounds are highly selective partial agonists or antagonists at human Corticotropin-Releasing Factor 1 (CRF1) receptors and are useful in the diagnosis and treatment of treating stress related disorders such as post trumatic stress disorder (PTSD) as well as depression, headache and anxiety.

9 Claims, No Drawings

CERTAIN PYRROLOPYRIDINE DERIVATIVES; NOVEL CRF1 SPECIFIC LIGANDS

"This is a continuation of application Ser. No. 09/368,541, filed Aug. 5, 1999, now U.S. Pat. No. 6,133,282, which is a continuation of application Ser. No. 08/542,854, filed Oct. 13, 1995, now U.S. Pat. No. 5,955,613."

BACKGROUND (IF THE INVENTION

1. Field of the Invention

This invention relates to novel substituted pyrrolopyridine derivatives which selectively bind to Corticotropin-Releasing Factor (CRF) receptors. More specifically, it relates to tetrahydro-5H-pyrido[2,3-b]indol-4-amines, 9H-pyrido[2,3-b]indol-4-amines, and 1H-pyrrolo[2,3-b]pyridin-4-amines, and their use as antagonists of Corticotropin-Releasing Factor in the treatment of various disease states.

2. Description of the Related Art

Corticotropin-releasing factor (CRF) antagonists are mentioned in U.S. Pat. Nos. 4,605,642 and 5,063,245 referring to peptides and pyrazoline derivatives, respectively. The importance of CRF antagonists is described in the literature, for example, as discussed in U.S. Pat. No. 5,063,245, which is incorporated herein by reference in its entirety. CRF antagonists are considered effective in the treatment of a wide range of diseases including stress-related illnesses, such as stress-induced depression, anxiety, and headache. Other diseases considered treatable with CRF antagonists are discussed in U.S. Pat. No. 5,063,245 and Pharm. Rev., 4: 425–473 (1991).

International application WO 9413676 A1 discloses pyrrolo[2,3-d]pyrimidines as having Corticotropin-Releasing Factor antagonist activity. J. Het. Chem. 9, 1077 (1972) describes the synthesis of 9-Phenyl-pyrrolo[3,2-d]pyrimidines.

SUMMARY OF THE INVENTION

This invention provides novel compounds of Formula I which interact with CRF receptors. Further, the invention provides pharmaceutical compositions comprising compounds of Formula I. It further relates to the use of such compounds and compositions in treating treating stress related disorders such as post traumatic stress disorder (PTSD) as well as depression, headache and anxiety. Accordingly, a broad embodiment of the invention is directed to a compound of Formula I:

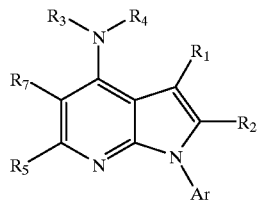

I wherein
- Ar is optionally substituted aryl or heteroaryl;
- $R_1$ is hydrogen or alkyl;
- $R_7$ is hydrogen or alkyl
- $R_2$ is hydrogen, halogen, alkyl or alkoxy; or
- $R_1$ and $R_2$ taken together with the ring to which they are attached form a 5–9 membered saturated or aromatic ring optionally having a hetero atom selected from oxygen, sulfur or nitrogen;
- $R_3$ and $R_4$ are independently hydrogen, alkyl, cycloalkyl, aryl or heteroaryl groups; or
- $R_3$ and $R_4$ together with the nitrogen atom to which they are attached form a 5–8 membered ring; and
- $R_5$ is hydrogen, halogen, straight or branched chain lower alkyl having 1–6 carbon atoms, or straight or branched chain lower alkoxy or thioalkoxy having 1–6 carbon atoms.

The compounds of the invention are highly selective partial agonists or antagonists at CRF receptors and are useful in the diagnosis and treatment of stress related disorders such as post trumatic stress disorder (PRSD) as well as depression and anxiety.

Thus, the invention provides compounds, including pharmaceutically acceptable salts of the compounds of formula I, and pharmaceutical compositions for use in treating disease states associated with Corticotropin-Releasing Factor. The invention further provides methods including animal models relevant to the evaluation of the interaction of the compounds of the invention with CRF receptors. This interaction results in the pharmacological activities of these compounds.

DETAILED DESCRIPTION OF THE INVENTION

In addition to the novel compounds of the instant invention described by general formula I above, the invention encompasses compounds of formula IA:

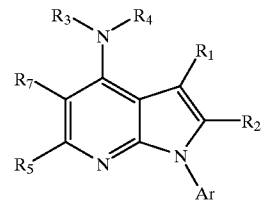

IA wherein
- Ar is phenyl, 2-, 3-, - or 4-pyridyl, 2- or 3-thienyl, 4- or 5-pyrimidinyl, each of which is monosubstituted or optionally di- or trisubstituted with halogen, hydroxy, lower alkyl, or lower alkoxy, provided that at least one of the ortho positions of Ar is substituted;
- $R_1$ is hydrogen or lower alkyl;
- $R_7$ is hydrogen or alkyl;
- $R_2$ is hydrogen, halogen, lower alkyl, lower alkoxy, or thioalkoxy; or
- $R_1$ and $R_2$ taken together represent —$(CH_2)_n$—A—$(CH_2)_m$— where n is 2, 3 or 4, A is methylene, oxygen, sulfur or $NR_6$, wherein $R_6$ is hydrogen or lower alkyl, and m is 0, 1 or 2; or
- $R_1$ and $R_2$ taken together represent —CH=E—CH=CH—, where E is CH or N;
- $R_3$ and $R_4$ are not both hydrogen and independently represent
  hydrogen, lower alkyl, phenyl, 2-, 3-, or 4-pyridyl, 2- or 3-thienyl or 2-, 4-, or 5-pyrimidinyl, each of which is optionally mono- or disubstituted with halogen, hydroxy, lower alkyl, or lower alkoxy;
  phenylalkyl, 2-, 3-, or 4-pyridylalkyl, 2- or 3-thienylalkyl, or 2-, 4- or 5-pyrimidinyl alkyl, where each alkyl is lower alkyl;

cycloalkyl having 3–8 carbon atoms, cycloalkyl lower alkyl, 2-hydroxyethyl or 3-hydroxypropyl, each of which is optionally mono or disubstituted with lower alkyl; or $R_3$ and $R_4$ taken together represent —$(CH_2)_n$—G—$(CH_2)_{\overline{m}}$ where n is 2, or 3;
m is 1,2or3; and
G is methylene, 1,2 phenylene, oxygen, sulfur or $NR_6$, wherein $R_6$ is lower alkyl, phenyl, 2-, 3-, or 4-pyridyl, 2- or 3-thienyl, or 2-, 4-, or 5-pyrimidinyl, or
$R_6$ is phenylalkyl, 2-, 3-, or 4-pyridylalkyl, 2- or 3-thienylalkyl, or 2-, 4- or 5-pyrimidinyl alkyl, where each alkyl is lower alkyl; and $R_5$ is hydrogen, halogen, lower alkyl, lower alkoxy, or thioalkoxy.

Preferred compounds of formula I are those where Ar is a disubstituted aryl or heteroaryl group having substituents in one ortho position and the para position. More preferred compounds of formula I are those where Ar is a trisubstituted aryl or heteroaryl group having substituents in both ortho positions and the para position, i.e., a 2, 4, 6-trisubstituted aryl group. The most preferred aryl group is phenyl. The preferred aryl substituents are lower alkyl groups or halogen, particularly fluorine. More preferred aryl substituents are methyl groups.

Other preferred compounds of formula I are those where the $NR_3R_4$ group is a disubstituted amino group, e.g., dialkyl amino. A particularly preferred $NR_3R_4$ group is dipropylamino.

In compounds of formula I, $R_5$ is preferably lower alkyl and, more preferably, methyl; and $R_7$ is preferably hydrogen.

In still other preferred compounds of formula I, $R_1$ and $R_2$ taken together represent —$(CH_2)_n$—A—$(CH_2)_m$— where n is 2, 3 or 4, A is methylene, oxygen, sulfur or NMe, and m is 0, 1 or 2.

The invention further provides compounds of formula II

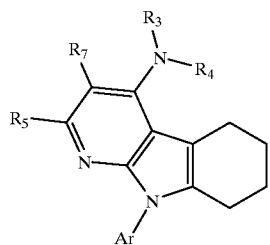

II wherein
Ar is phenyl, 2-, 3, - or 4-pyridyl, 2- or 3-thienyl, 4- or 5-pyrimidinyl, each of which is monosubstituted or optionally di- or trisubstituted with halogen, hydroxy, lower alkyl, or lower alkoxy, provided that at least one of the ortho positions of Ar is substituted;
$R_7$ is hydrogen or alkyl;
$R_3$ and $R_4$ are not both hydrogen and independently represent
hydrogen, lower alkyl, phenyl, 2-, 3-, or 4pyridyl, 2- or 3-diienyl or 2-, 4-, or 5-pyrimidinyl, each of which is optionally mono- or disubstituted with halogen, hydroxy, lower alkyl, or lower alkoxy;
phenylalkyl, 2-, 3-, or 4-pyridylalkyl, 2- or 3-thienylalkyl, or 2-, 4- or 5-pyrimidinyl alkyl, where each alkyl is lower alkyl;

cycloalkyl having 3-8 carbon atoms, cycloalkyl lower alkyl, 2-hydroxyethyl or 3-hydroxypropyl, each of which is optionally mono or disubstituted with lower alkyl; or $R_3$ and $R_4$ taken together represent —$(CH_2)_n$—G—$(CH_2)_{\overline{m}}$ where n is 2, or 3;
m is 1, 2 or 3; and
G is methylene, 1,2 phenylene, oxygen, sulfur or $NR_6$, wherein $R_6$ is lower alkyl, phenyl, 2-, 3-, or 4-pyridyl, 2- or 3-thienyl, or 2-, 4-, or 5-pyrimidinyl, or
$R_6$ is phenylalkyl, 2-, 3-, or 4-pyridylalkyl, 2- or 3-thienylalkyl, or 2-, 4- or 5-pyrimidinyl alkyl, where each alkyl is lower alkyl; and $R_5$ is hydrogen, halogen, lower alkyl, lower alkoxy, or thioalkoxy.

Preferred compounds of formula II are those where Ar is a disubstituted aryl or heteroaryl group having substituents in one ortho position and the para position. More preferred compounds of formula II are those where Ar is a trisubstituted aryl or heteroaryl group having substituents in both ortho positions and the para position, i.e., a 2, 4, 6-trisubstituted aryl group. The most preferred aryl group is phenyl. The preferred aryl substituents arc lower alkyl groups or halogen, particularly fluorine. More preferred aryl substituents are methyl groups.

Other preferred compounds of formula II are those where the $NR_3R_4$ group is a disubstituted amino group, e.g., dialkyl amino. A particularly preferred $NR_3R_4$ group is dipropylamino.

In yet other preferred compounds of formula II, $R_7$ is hydrogen.

The invention further provides compounds of formula III

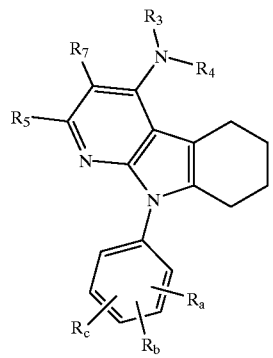

III wherein
$R_a$, $R_b$, and $R_c$ independently represent halogen, hydroxy, lower alkyl, or lower alkoxy;
$R_7$ is hydrogen or alkyl;
$R_3$ and $R_4$ are independently represent
hydrogen, lower alkyl, phenyl, 2-, 3-, or 4-pyridyl, 2- or 3-thienyl or 2-, 4-, or 5-pyrimidinyl, each of which is optionally mono- or disubstituted with halogen, hydroxy, lower alkyl, or lower alkoxy;
phenylalkyl, 2-, 3-, or 4-pyridylalkyl, 2- or 3-thienylalkyl, or 2-, 4- or 5-pyrimidinyl alkyl, where each alkyl is lower alkyl;
cycloalkyl having 3–8 carbon atoms, cycloalkyl lower alkyl, 2-hydroxyethyl or 3-hydroxypropyl, each of which is optionally mono or disubstituted with lower alkyl; or R$_3$ and R$_4$ taken together represent —(CH$_2$)$_n$—G—(CH$_2$)$_{\overline{m}}$ where n is 2, or 3;
m is 1,2or 3; and
G is methylene, 1,2 phenylene, oxygen, sulfur or NR$_6$, wherein R$_6$ is lower alkyl, phenyl, 2-, 3-, or 4-pyridyl, 2- or 3-thienyl, or 2-, 4-, or 5-pyrimidinyl, or
R$_6$ is phenylalkyl, 2-, 3-, or 4-pyridylalkyl, 2- or 3-thienylalkyl, or 2-, 4- or 5-pyrimidinyl alkyl, where each alkyl is lower alkyl; and R$_5$ is hydrogen, halogen, lower alkyl, lower alkoxy, or thioalkoxy.

Preferred compounds of formula III are those where at least one of R$_a$, R$_b$, or R$_c$ is present in one of the two ortho positions of the phenyl group to which they are attached. More preferred compounds of formula III are those where at least two of R$_a$, R$_b$, or R$_c$ are present in one ortho position and the para position. Still more preferred compounds of formula III are those where the R$_a$, R$_b$, or R$_c$ substituents are present in both ortho positions and the para position, i.e., a 2, 4, 6-trisubstituted phenyl group. The preferred R$_a$, R$_b$, or R$_c$ substituents are lower alkyl groups or halogen, particularly fluorine. More preferred aryl substituents are methyl groups.

Other preferred compounds of formula III are those where the NR$_3$R$_4$ group is a disubstituted amino group, e.g., dialkyl amino. A particularly preferred NR$_3$R$_4$ group is dipropylamino.

In still other preferred compounds of formula III, R$_7$ is hydrogen.

The invention further provides compounds of formula IV

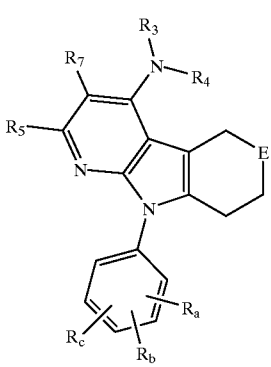

IV wherein
E represents CH$_2$ or NR$_6$, wherein R$_6$ is hydrogen or lower alkyl;
R$_7$ is hydrogen or alkyl;
R$_a$, R$_b$, and R$_c$ independently represent halogen, hydroxy, lower alkyl, or lower alkoxy;
R$_3$ and R$_4$ are independently represent
hydrogen, lower alkyl, phenyl, 2-, 3-, or 4-pyridyl, 2- or 3-thienyl or 2-, 4-, or 5-pyrimidinyl, each of which is optionally mono- or disubstituted with halogen, hydroxy, lower alkyl, or lower alkoxy;
phenylalkyl, 2-, 3-, or 4-pyridylalkyl, 2- or 3-thienylalkyl, or 2-, 4- or 5-pyrimidinyl alkyl, where each alkyl is lower alkyl;
cycloalkyl having 3–8 carbon atoms, cycloalkyl lower alkyl, 2-hydroxyethyl or 3-hydroxypropyl, each of which is optionally mono or disubstituted with lower alkyl; or R$_3$ and R$_4$ taken together represent —(CH$_2$)$_n$—G—(CH$_2$)$_{\overline{m}}$ where n is 2, or 3;
m is 1, 2 or 3; and
G is methylene, 1,2 phenylene, oxygen, sulfur or NR$_6$, wherein R$_6$ is lower alkyl, phenyl, 2-, 3-, or 4-pyridyl, 2- or 3-thienyl, or 2-, 4-, or 5-pyrimidinyl, or
R$_6$ is phenylalkyl, 2-, 3-, or 4pyridylalkyl, 2- or 3-thienylalkyl, or 2-, 4- or 5-pyrimidinylalkyl, where each alkyl is lower alkyl; and R$_5$ is hydrogen, halogen, lower alkyl, lower alkoxy, or thioalkoxy.

Preferred compounds of formula IV are those where at least one of R$_a$, R$_b$, or R$_c$ is present in one of the two ortho positions of the phenyl group to which they are attached. More preferred compounds of formula IV are those where at least two of R$_a$, R$_b$, or R$_c$ are present in one ortho position and the para position. Still more preferred compounds of formula IV are those where the R$_a$, R$_b$, or R$_c$ substituents are present in both ortho positions and the para position, i.e., a 2, 4, 6-trisubstituted phenyl group. The preferred R$_a$, R$_b$, or R$_c$ substituents are lower alkyl groups or halogen, particularly fluorine. More preferred aryl substituents are methyl groups.

Other preferred compounds of formula IV are those where the NR$_3$R$_4$ group is a disubstituted amino group, e.g., dialkyl amino. A particularly preferred NR$_3$R$_4$ group is dipropylamino. In preferred compounds of formula IV, E represents carbon.

In other preferred compounds of formula IV, R$_7$ is hydrogen.

The invention further provides compounds of formula V

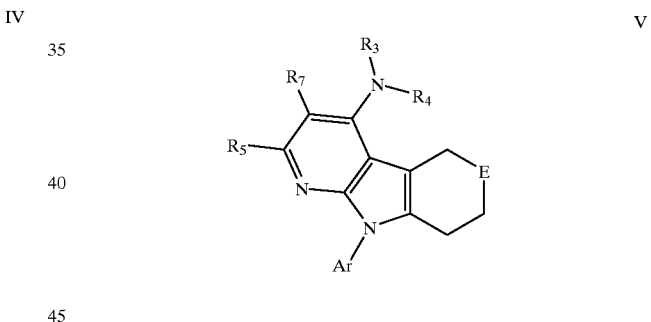

V wherein
E represents CH$_2$ or NR$_6$, wherein R$_6$ is hydrogen or lower alkyl;
R$_7$ is hydrogen or alkyl;
Ar is phenyl, 2-, 3,- or 4-pyridyl, 2- or 3-thienyl, 4- or 5-pyrimidinyl, each of which is monosubstituted or optionally di- or trisubstituted with halogen, hydroxy, lower alkyl, or lower alkoxy, provided that at least one of the ortho positions of Ar is substituted;
R$_3$ and R$_4$ are not both hydrogen and independently represent
hydrogen, lower alkyl, phenyl, 2-, 3-, or 4pyridyl, 2- or 3-thienyl or 2-, 4-, or 5-pyrimidinyl, each of which is optionally mono- or disubstituted with halogen, hydroxy, lower alkyl, or lower alkoxy;
phenylalkyl, 2-, 3-, or 4-pyridylalkyl, 2- or 3-thienylalkyl, or 2-, 4- or 5-pyrimidinyl alkyl, where each alkyl is lower alkyl;
cycloalkyl having 3–8 carbon atoms, cycloalkyl lower alkyl, 2-hydroxyethyl or 3-hydroxypropyl, each of which is optionally mono or disubstituted with lower alkyl; or R₃ and R₄ taken together represent —(CH₂)ₙ—G—(CH₂)ₘ
  where n is 2, or 3;
  m is 1, 2 or 3; and
  G is methylene, 1,2 phenylene, oxygen, sulfur or NR₆,
    wherein R₆ is lower alkyl, phenyl, 2-, 3-, or
    4-pyridyl, 2- or 3-thienyl, or 2-, 4-, or
    5-pyrimidinyl, or
    R₆ is phenylalkyl, 2-, 3-, or 4-pyridylalkyl, 2- or
    3-thienylalkyl, or 2-, 4- or 5-pyrimidinylalkyl,
    where each alkyl is lower alkyl; and
R₅ is hydrogen, halogen, lower alkyl, lower alkoxy, or thioalkoxy.

Preferred compounds of formula V are those where Ar is a disubstituted aryl or heteroaryl group having substituents in one ortho position and the para position. More preferred compounds of formula V are those where Ar is a trisubstituted aryl or heteroaryl group having substituents in both ortho positions and the para position, i.e., a 2, 4, 6-trisubstituted aryl group. The most preferred aryl group is phenyl. The preferred aryl substituents are lower alkyl groups or halogen, particularly fluorine. More preferred aryl substituents are methyl groups.

Other preferred compounds of formula V are those where the NR₃R₄ group is a disubstituted amino group, e.g., dialkyl amino. A particularly preferred NR₃R₄ group is dipropylamino. In preferred compounds of formula V, E represents carbon.

Yet other preferred compounds of formula V are those where R₇ is hydrogen.

The invention further provides compounds of formula VI

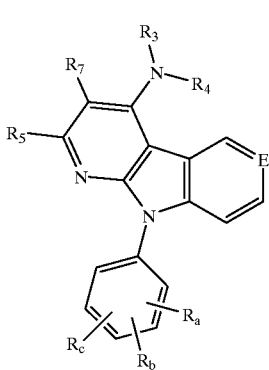

VI wherein
  E represents CH₂ or NR₆, wherein R₆ is hydrogen or lower alkyl;
  Rₐ, R_b, and R_c independently represent halogen, hydroxy, lower alkyl, or lower alkoxy;
  R₇ is hydrogen or alkyl;
  R₃ and R₄ are independently represent
    hydrogen, lower alkyl, phenyl, 2-, 3-, or 4-pyridyl, 2- or 3-thienyl or 2-, 4, or 5-pyrimidinyl, each of which is optionally mono- or disubstituted with halogen, hydroxy, lower alkyl, or lower alkoxy;
    phenylalkyl, 2-, 3-, or 4-pyridylalkyl, 2- or 3-thienylalkyl, or 2-, 4- or 5-pyrimidinyl alkyl, where each alkyl is lower alkyl;
    cycloalkyl having 3–8 carbon atoms, cycloalkyl lower alkyl, 2-hydroxyethyl or 3-hydroxypropyl, each of which is optionally mono or disubstituted with lower alkyl; or
  R₃ and R₄ taken together represent —(CH₂)ₙ—G—(CH₂)ₘ
    where n is 2, or 3;
    m is 1, 2 or 3; and
    G is methylene, 1,2 phenylene, oxygen, sulfur or NR₆,
      wherein R₆ is lower alkyl, phenyl, 2-, 3-, or 4pyridyl, 2- or 3-thienyl, or 2-, 4-, or ⁵-pyrimidinyl, or
      R₆ is phenylalkyl, 2-, 3-, or ⁴-pyridylalkyl, 2- or ³-thienylalkyl, or 2-, 4- or 5-pyrimidinylalkyl, where each alkyl is lower alkyl; and
  R₅ is hydrogen, halogen, lower alkyl, lower alkoxy, or thioalkoxy.

Preferred compounds of formula VI are those where at least one of Rₐ, R_b, or R_c is present in one of the two ortho positions of the phenyl group to which they are attached. More preferred compounds of formula VI are those where at least two of Rₐ, R_b, or R_c are present in one ortho position and the para position. Still more preferred compounds of formula VI are those where the Rₐ, R_b, or R_c substituents are present in both ortho positions and the para position, i.e., a 2, 4, 6-trisubstituted phenyl group. The preferred Rₐ, R_b, or R_c substituents are lower alkyl groups or halogen, particularly fluorine. More preferred aryl substituents are methyl groups.

Other preferred compounds of formula VI are those where the NR₃R₄ group is a disubstituted amino group, e.g., dialkyl amino. A particularly preferred NR₃R₄ group is dipropylamino. In preferred compounds of formula VI, E represents carbon.

In yet other referred compounds of formula VI, R₇ is hydrogen.

The invention further provides compounds of formula VII

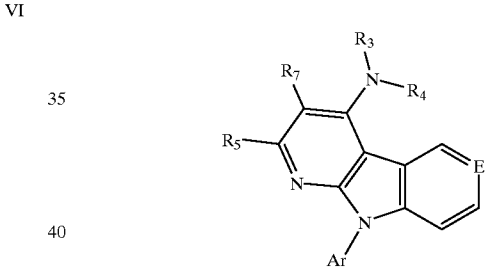

VII wherein
  E represents CH₂ or NR₆, wherein R₆ is hydrogen or lower alkyl;
  Ar is phenyl, 2-, 3,- or 4-pyridyl, 2- or 3-thienyl, 4- or 5-pyrimidinyl, each of which is monosubstituted or optionally di- or trisubstituted with halogen, hydroxy, lower alkyl, or lower alkoxy, provided that at least one of the ortho positions of Ar is substituted;
  R₇ is hydrogen or alkyl;
  R₃ and R₄ are not both hydrogen and independently represent
    hydrogen, lower alkyl, phenyl, 2-, 3-, or 4pyridyl, 2- or 3-thienyl or 2-, 4-, or 5-pyrimidinyl, each of which is optionally mono- or disubstituted with halogen, hydroxy, lower alkyl, or lower alkoxy;
    phenylalkyl, 2-, 3-, or 4-pyridylalkyl, 2- or 3-thienylalkyl, or 2-, 4- or 5-pyrimidinyl alkyl, where each alkyl is lower alkyl;
    cycloalkyl having 3–8 carbon atoms, cycloalkyl lower alkyl, 2-hydroxyethyl or 3-hydroxypropyl, each of which is optionally mono or disubstituted with lower alkyl; or
  R₃ and R₄ taken together represent —(CH₂)ₙ—G—(CH₂)ₘ where n is 2, or 3;
m is 1, 2 or 3; and
2G is methylene, 1,2 phenylene, oxygen, sulfur or $NR_6$,
wherein $R_6$ is lower alkyl, phenyl, 2-, 3-, or 4pyridyl, 2- or 3-thienyl, or 2-, 4-, or 5-pyrimidinyl, or
$R_6$ is phenylalkyl, 2-, 3-, or 4pyridylalkyl, 2- or 3-thienylalkyl, or 2-, 4- or 5-pyrimidinylalkyl, where each alkyl is lower alkyl; and
$R_5$ is hydrogen, halogen, lower alkyl, lower alkoxy, or thioalkoxy.

Preferred compounds of formula VI are those where Ar is a disubstituted aryl or heteroaryl group having substituents in one ortho position and the para position. More preferred compounds of formula VII are those where Ar is a trisubstituted aryl or heteroaryl group having substituents in both ortho positions and the para position, i.e., a 2, 4, 6-trisubstituted aryl group. The most preferred aryl group is phenyl. The preferred aryl substituents are lower alkyl groups or halogen, particularly fluorine. More preferred aryl substituents are methyl groups.

Other preferred compounds of formula VII are those where the $NR_3R_4$ group is a disubstituted amino group, e.g., dialkyl amino. A particularly preferred $NR_3R_4$ group is dipropylamino. In preferred compounds of formula VII, E represents carbon.

In still other compounds of formula VII, $R_7$ is hydrogen.
The invention also provides compounds of formula VIII:

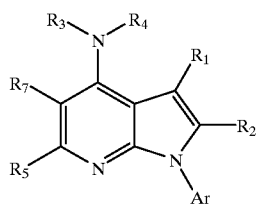

VIII wherein
$R_1$ is hydrogen or lower alkyl;
$R_2$ is hydrogen, halogen, lower alkyl, lower alkoxy, or thioalkoxy;
Ar is phenyl, 2-, 3,- or 4-pyridyl, 2- or 3-thienyl, 4- or 5-pyrimidinyl, each of which is monosubstituted or optionally di- or trisubstituted with halogen, hydroxy, lower alkyl, or lower alkoxy, provided that at least one of the ortho positions of Ar is substituted;
$R_7$ is hydrogen or alkyl;
$R_3$ and $R_4$ are not both hydrogen and independently represent
hydrogen, lower alkyl, phenyl, 2-, 3-, or 4pyridyl, 2- or 3-thienyl or 2-, 4, or 5-pyrimidinyl, each of which is optionally mono- or disubstituted with halogen, hydroxy, lower alkyl, or lower alkoxy;
phenylalkyl, 2-, 3-, or 4-pyridylalkyl, 2- or 3-thienylalkyl, or 2-, 4- or 5-pyridinyl alkyl, where each alkyl is lower alkyl;
cycloalkyl having 3–8 carbon atoms, cycloalkyl lower alkyl, 2-hydroxyethyl or 3-hydroxypropyl, each of which is optionally mono or disubstituted with lower alkyl; or
$R_3$ and $R_4$ taken together represent $-(CH_2)_n-G-(CH_2)_{\overline{m}}$
where n is 2, or 3;
m is 1, 2 or 3; and
G is methylene, 1,2 phenylene, oxygen, sulfur or $NR_6$, wherein $R_6$ is lower alkyl, phenyl, 2-, 3-, or 4-pyridyl, 2- or 3-thienyl, or 2-, 4-, or 5-pyrimidinyl, or
$R_6$ is phenylalkyl, 2-, 3-, or 4-pyridylalkyl, 2- or 3-thienylalkyl, or 2-, 4- or 5-pyrimidinylalkyl, where each alkyl is lower alkyl; and
$R_5$ is hydrogen, halogen, lower alkyl, lower alkoxy, or thioalkoxy.

Preferred compounds of formula VIII are those where Ar is a disubstituted aryl or heteroaryl group having substituents in one ortho position and the para position. More preferred compounds of formula VIII are those where Ar is a trisubstituted aryl or heteroaryl group having substituents in both ortho positions and the para position, i.e., a 2, 4, 6-trisubstituted aryl group. The most preferred aryl group is phenyl The preferred aryl substituents are lower alkyl groups or halogen, particularly fluorine. More preferred aryl substituents are methyl groups.

Other preferred compounds of formula VIII are those where the $NR_3R_4$ group is a disubstituted amino group, e.g., dialkyl amino. A particularly preferred $NR_3R_4$ group is dipropylamino.

In still other preferred compounds of formula VIII, $R_1$ and $R_2$ are independently alkyl groups. In more preferred compounds of formula VIII, $R_1$ and $R_2$ are both methyl.

In the compounds of the invention, preferred $NR_3R_4$ groups include the following:

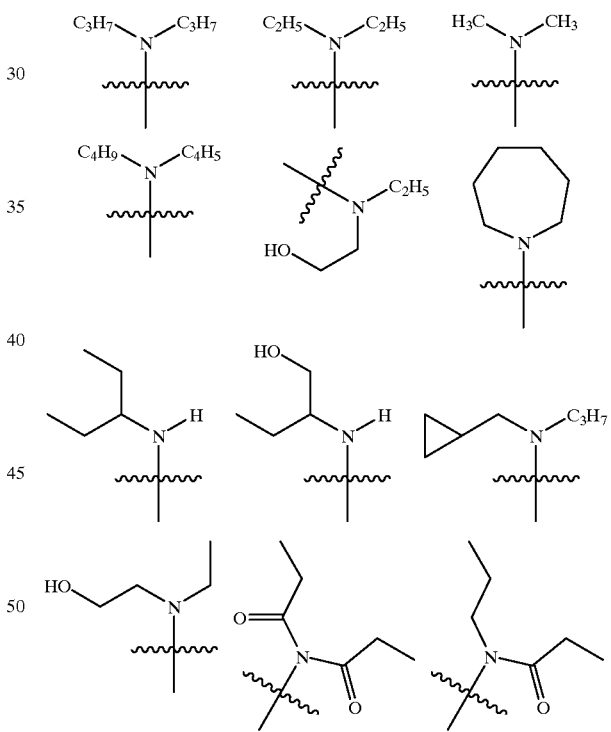

Representative compounds of the present invention, which are encompassed by Formula I, include, but are not limited to the compounds in FIG. I and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By aryl or "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy.

By aryl or "Ar" is also meant heteroaryl groups where heteroaryl is defined as 5, 6, or 7 membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

By alkyl and lower alkyl is meant straight and branched chain alkyl groups having from 1–6 carbon atoms. Specific non-limiting examples of alkyl groups are methyl, ethyl, propyl, isopropyl, n-butyl, isobutyl, tert-butyl, sec-butyl, neopentyl and n-pentyl.

By lower alkoxy and alkoxy is meant straight and branched chain alkoxy groups having from 1–6 carbon atoms.

By thioalkoxy or alkylthio is meant a group of the formula —S-alkyl, where the alkyl is straight or branched chain alkyl having from 1–6 carbon atoms.

By halogen is meant fluorine, chlorine, bromine and iodine.

The pharmaceutical utility of compounds of this invention are indicated by the following assay for CRF receptor activity.

Assay for CRF Receptor Binding Activity

CRF receptor binding was performed using a modified version of the assay described by Grigoriadis and De Souza (Biochemical, Pharmacological, and Autoradiographic Methods to Study Corticotropin-Releasing Factor Receptors. *Methods in Neurosciences*, Vol. 5, 1991). Membrane pellets containing CRF receptors were resuspended in 50 mM Tris buffer pH 7.7 containing 10 mM $MgCl_2$ and 2mM EGTA and centrifuged for 10 minutes at 48000 g. Membranes were washed again and brought to a final concentration of 1500 ug/ml in binding buffer (Tris buffer above with 0.1% BSA, 0.15 mM bacitracin and 0.01 mg/ml aprotinin.). For the binding assay, 100 ul of the membrane preparation was added to 96 well microtube plates containing 100 ul of 125I-CRF (SA 2200 Ci/mmol , final concentration of 100 pM) and 50 ul of drug. Binding was carried out at room temperature for 2 hours. Plates were then harvested on a Brandel 96 well cell harvester and filters were counted for gamma emissions on a Wallac 1205 Betaplate liquid scintillation counter. Non specific binding was defined by 1 uM cold CRF. $IC_{50}$ values were calculated with the non-linear curve fitting program RS/1 (BBN Software Products Corp., Cambridge, Maas.). The $IC_{50}$ for Compound 1 of this invention is 0.011 $\mu M$.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative illustration of methods suitable for the preparation of compounds of the present invention is shown in Schemes I and II. Those having skill in the art will recognize that the starting materials may be varied and additional steps employed to produce compounds encompassed by the present invention.

Scheme I

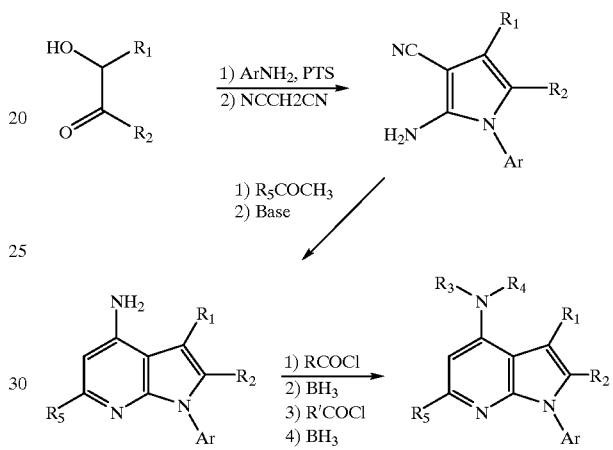

wherein Ar, $R_1$, $R_2$, $R_3$, $R_4$, and $R_5$ are as defined above for formula I.

In the case where a desired compound of the invention that may be prepared according to Scheme I includes $R_7$ as alkyl, the intermediate 2-amino-1-aryl-3-cyanopyrrole is reacted with base and a compound of the formula $R_5COCH_2R_7$, where $R_7$ is alkyl.

Scheme II

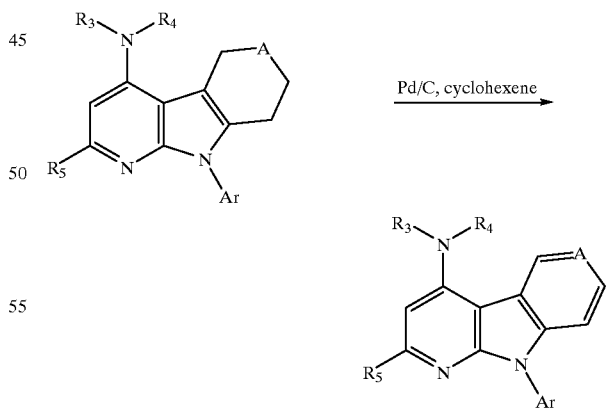

where A is NH or $CH_2$, and Ar, $R_3$, $R_4$, and $R_5$ are as defined above for formula I.

As mentioned above, where a desired compound of the invention that may be prepared according to Scheme II includes $R_7$ as alkyl, the intermediate 2-amino-1-aryl-3-cyanopyrrole is reacted with base and a compound of the formula $R_5COCH_2R_7$, where $R_7$ is alkyl.

The disclosures in this application of all articles and references, including patents, are incorporated herein by reference.

One skilled in the art will recognize that modifications may be made in the present invention without deviating from the spirit or scope of the invention. The invention is illustrated further by the following examples which are not to be construed as limiting the invention or scope of the specific procedures or compositions described herein.

EXAMPLE IA

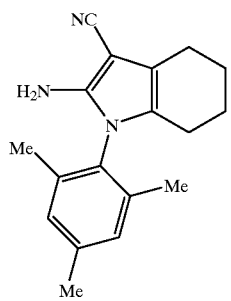

1a

A mixture of 2,4,6-trimethylaniline (10.5 g 78 mmol), 2-hydroxycyclohexanone dimer (8.9 g, 39 mmol) and pTsOH (44 mg) is refluxed in 100 mL of toluene. Water is removed using a Dean-Stark apparatus. After 2 hours the solution is cooled and malononitrile (5.2 g) dissolved in 20 mL toluene is added. The mixture is refluxed for another 8 hours after which the solvent is removed under reduced pressure. The crude product is triturated with ether and some ethanol, and collected by filtration as a tan solid to afford aminonitrile 1a.

EXAMPLE IB

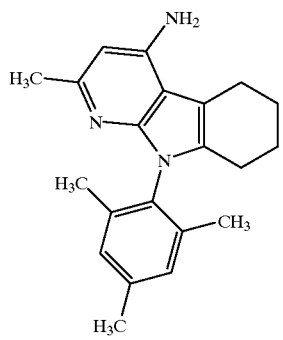

1b

Aminonitrile 1a (1.1 g, 4.0 mmol) prepared above is stirred with anhydrous acetone (1.5 mL), pTsOH (10 mg) and 4A molecular sieves (1 g) in 10 mL benzene at 60° C. for 10 hours. The mixture is then filtered through celite pretreated with triethylamine. The volatile solvents are removed under reduced pressure. The residual material is dissolved in 20 mL THF and treated with lithium diisopropylamide (2.0 M, 4 mL) under ice cooling. After 1 hour the mixture is poured into water and extracted with ethyl acetate. The organic layer is subsequently extracted with 5% hydrochloric acid. The aqueous layer is made alkaline with 10N sodium hydroxide and extracted with dichloromethane. The extract is washed with water, dried over sodium sulfate, and concentrated to afford 2-Methyl-6,7,8,9-tetrahydro-9-(2,4,6-trimethylphenyl)-5H-pyrido[2,3-b]indol-4-amine 1b as a white solid.

EXAMPLE IC

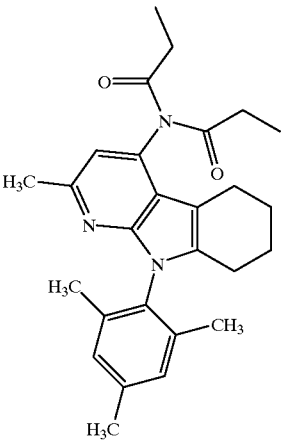

1c

2-Methyl-6,7,8,9-tetrahydro-9-(2,4,6-trimethylphenyl)-5H-pyrido[2,3-b]indol-4-amine (1b) (470 mg) dissolved in 10 mL dichloroethane is refluxed for 3 hours with propionyl chloride (0.5 mL). The. residual reagents are evaporated under reduced pressure. The crude product is partitioned between aqueous sodium carbonate solution and dichloromethane. The organic extract is dried over sodium sulfate and concentrated. The solid, diacylated product is triturated with hexanes and collected by filtration to afford N,N-Dipropionyl-2-methyl-6,7,8,9-tetrahydro-9-(2,4,6-trimethyl phenyl)-5H-pyrido[2,3-b]indol-4-amine 1c as a white solid.

EXAMPLE ID

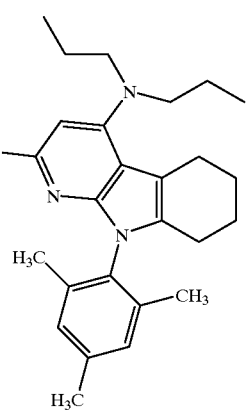

Compound 1

N,N-Dipropionyl-2-methyl-9-(2,4,6-trimethylphenyl)-5H-pyrido[2,3-b]indol-4-amine 1c (312 mg) is refluxed in 8 mL THF with borane-methylsulfide complex (10 M, 1.2 mL) for 10 hours. After cooling the solution, it is carefully quenched with 5 mL of methanol. The resulting solution is refluxed for another 2 hours and then concentrated The dialkylamine product is purified on silica gel using 20% ethyl acetate in hexanes as eluant to afford N,N-Dipropyl-2-methyl-6,7,8,9-tetrahydro-9-(2,4,6-trimethylphenyl)-5H- pyrido[2,3-b]indol4-amine (Compound 1) as a white solid, m.p.: 117–118° C.

EXAMPLE II

The following compounds are prepared essentially according to the procedures described in Examples IA–D:

a) N-Propyl-N-cyclopropylmethyl-2-methyl-6,7,8,9-tetrahydro-9-(2,4,6-trimethylphenyl)-5H-pyrido[2,3-b]indol-4-amine (Compound 2).

b) N-Propyl-N-cyclopropylmethyl-2-methyl-9-(2,4,6-trimethylphenyl)-9H-pyrido[2,3-b]indol-4-amine (Compound 3):

Compound 3

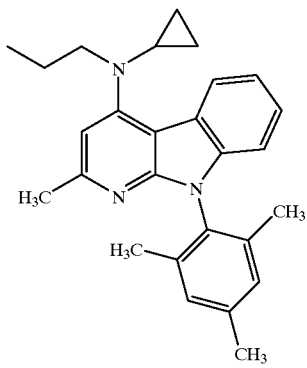

c) N-Butyl-N-Ethyl-2-methyl-6,7,8,9-tetrahydro-9-(2,4,6-trimethylphenyl)-5H-pyrido[2,3-b]indol-4-amine (Compound 4).

d) N,N-Dipropyl-2-methyl-9-(2,4,6-trimethylphenyl)-9H-pyrido[2,3-b]indol-4-amine (Compound 5).

e) N-Butyl-N-Ethyl-2-methyl-9-(2,4,6-trimethylphenyl)-9H-pyrido[2,3-b]indol-4-amine (Compound 6).

f) N,N-Dipropyl- 1-(2,4,6trimethylphenyl)-2,5,6-trimethyl- IH-pyrrolo[2,3-b]pyridin-4-amine (Compound 7).

g) N-Cyclopropylmethyl-N-propyl-1-(2,4,6-trimethylphenyl)-2,5,6-trimethyl-1H-pyrrolo[2,3-b]pyridin-4-amine (Compound 8).

Compound 8

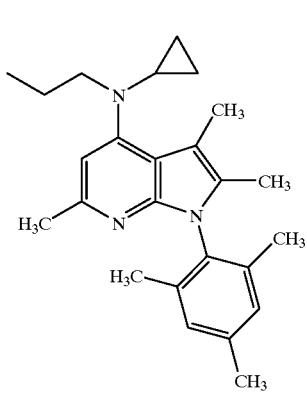

h) N-Butyl-N-ethyl- 1-(2,4,6-trimethylphenyl)-2,5,6-trimethyl- 1H-pyrrolo[2,3-b]pyridin-4-amine (Compound 9).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A pharmaceutical composition comprising a pharmaceutically acceptable carrier and a compound of the formula:

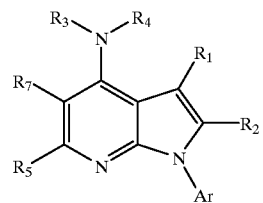

or the pharmaceutically acceptable salts thereof wherein

Ar is phenyl, 2-, 3-, or 4-pyridyl, 2-or 3-thienyl, 4-or 5-pyrimidinyl, each of which is monosubstituted, or optionally di- or trisubstituted with halogen, hydroxy, lower alkyl, or lower alkoxy, provided that at least one of the ortho positions of Ar is substituted;

$R_7$ is hydrogen or alkyl;

$R_1$ and $R_2$ taken together represent —CH=A—CH=CH—, where A is CH or N;

$R_3$ and $R_4$ are not both hydrogen and independently represent hydrogen, lower alkyl, phenyl, 2-, 3-, or 4-pyridyl, 2-or 3-thienyl or 2-, 4-, or 5-pyrimidinyl, each of which is optionally mono- or disubstituted with halogen, hydroxy, lower alkyl, or lower alkoxy, phenylalkyl, 2-, 3-, or 4-pyridylalkyl, 2-or 3-thienylalkyl, or 2-, 4-, or 5-pyrimidinylalkyl, where each alkyl is lower alkyl, cycloalkyl having 3–8 carbon atoms, cycloalkyl lower alkyl, 2-hydroxyethyl or 3-hydroxypropyl, each of which is optionally mono or disubstituted with lower alkyl; or $R_3$ and $R_4$ taken together represent —$(CH_2)_n$—G—$(CH_2)_m$— where n is 2, or 3;

m is 1, 2, or 3; and

G is methylene, 1,2 phenylene, oxygen, sulfur or $NR_6$, wherein $R_6$ is lower alkyl, phenyl, 2-, 3-, or 4-pyridyl, 2- or 3-thienyl or 2-, 4-or 5-pyrimidinyl, or $R_6$ is phenylalkyl, 2-, 3-, or 4-pyridylalkyl, 2-or 3-thienylalkyl, or 2-, 4- or 5-pyrimidinylalkyl where each alkyl is lower alkyl; and $R_5$ is hydrogen, halogen, lower alkyl, lower alkoxy, or thioalkoxy.

2. A pharmaceutical composition comprising a pharmaceutically acceptable carrier and a compound of the formula

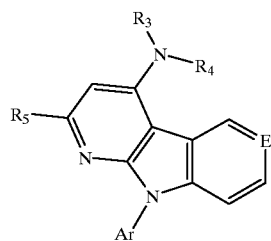

or a pharmaceutically acceptable salt thereof wherein
E represents CH or nitrogen;
Ar is phenyl, 2-, 3-, or 4-pyridyl, 2- or 3-thienyl, 4-or 5-pyrimidinyl, each of which is monosubstituted or optionally di- or trisubstituted with halogen, hydroxy, lower alkyl, or lower alkoxy, provided that at least one of the ortho positions of Ar is substituted;
$R_3$ and $R_4$ are not both hydrogen and independently represent
hydrogen, lower alkyl, phenyl, 2-, 3-, 4-pyridyl, 2-or 3-thienyl or 2-, 4-, or 5-pyrimidinyl, each of which is optionally mono- or disubstituted with halogen, hydroxy, lower alkyl, or lower alkoxy;
phenylalkyl, 2-, 3-, or 4-pyridylalkyl, 2-or 3-thienylalkyl, or 2-, 4-, or 5-pyrimidinylalkyl, where each alkyl is lower alkyl,
cycloalkyl having 3–8 carbon atoms, cycloalkyl lower alkyl, 2-hydroxyethyl or 3-hydroxypropyl, each of which is optionally mono or disubstituted with lower alkyl; and
$R_5$ is lower alkyl.

3. A pharmaceutical composition according to claim 2, wherein Ar is

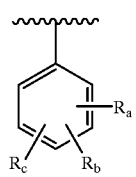

where $R_a$, $R_b$, and $R_c$ independently represent halogen, hydroxy, lower alkyl, or lower alkoxy.

4. A pharmaceutical composition according to claim 3, wherein Ar is

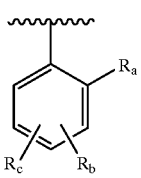

where $R_a$ represent halogen, hydroxy, lower alkyl, or lower alkoxy; $R_b$ and $R_c$ independently represents halogen, hydroxy, lower alkyl, or lower alkoxy.

5. A pharmaceutical composition according to claim 1, where the compound is N-Propyl-N-cyclopropylmethyl-2-methyl-9-(2,4,6-trimethylphenyl)-9H-pyrido[2,3-b]indol-4-amine or a pharmaceutically acceptable salt thereof.

6. A pharmaceutical composition according to claim 1, where the compound is N,N-Dipropyl-2-methyl-9-(2,4,6-trimethylphenyl)-9H-pyrido[2,3-b]indol-4-amine or a pharmaceutically acceptable salt thereof.

7. A pharmaceutical composition according to claim 1, where the compound is N-Butyl-N-Ethyl-2-methyl-9-(2,4,6-trimethylphenyl)-9H-pyrido[2,3-b]indol-4-amine or a pharmaceutically acceptable salt thereof.

8. A method for treatment of post traumatic stress disorder, depression or anxiety, which comprises administration to a patient in need thereof an effective amount of a compound of the formula:

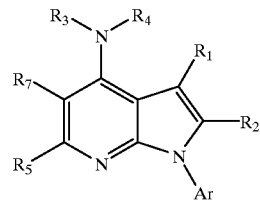

or the pharmaceutically acceptable salts thereof wherein

Ar is phenyl, 2-, 3-, or 4-pyridyl, 2-or 3-thienyl, 4-or 5-pyrimidinyl, each of which is monosubstituted, or optionally di- or trisubstituted with halogen, hydroxy, lower alkyl, or lower alkoxy, provided that at least one of the ortho positions of Ar is substituted;

$R_7$ is hydrogen or alkyl;

$R_1$ and $R_2$ taken together represent —CH=A—CH=CH—, where A is CH or N;

$R_3$ and $R_4$ are not both hydrogen and independently represent
hydrogen, lower alkyl, phenyl, 2-, 3-, or 4-pyridyl, 2-or 3-thienyl or 2-, 4-, or 5-pyrimidinyl, each of which is optionally mono- or disubstituted with halogen, hydroxy, lower alkyl, or lower alkoxy,
phenylalkyl, 2-, 3-, or 4-pyridylalkyl, 2-or 3-thienylalkyl, or 2-, 4-, or 5-pyrimidinylalkyl, where each alkyl is lower alkyl,
cycloalkyl having 3–8 carbon atoms, cycloalkyl lower alkyl, 2-hydroxyethyl or 3-hydroxypropyl, each of which is optionally mono or disubstituted with lower alkyl; or $R_3$ and $R_4$ taken together represent —$(CH_2)_n$—G—$(CH_2)_m$—
where n is 2, or 3;
m is 1, 2, or 3; and
G is methylene, 1,2 phenylene, oxygen, sulfur or $NR_6$, wherein $R_6$ is lower alkyl, phenyl, 2-, 3-, or 4-pyridyl, 2- or 3-thienyl or
2-, 4-or 5-pyrimidinyl, or
$R_6$ is phenylalkyl, 2-, 3-, or 4-pyridylalkyl, 2-or 3-thienylalkyl, or 2-, 4- or 5-pyrimidinylalkyl where each alkyl is lower alkyl; and $R_5$ is hydrogen, halogen, lower alkyl, lower alkoxy, or thioalkoxy.

9. A method for treatment of post traumatic stress disorder, depression or anxiety, which comprises administration to a patient in need thereof an effective amount of compound of the formula

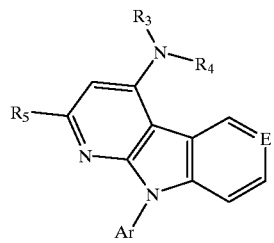

or a pharmaceutically acceptable salt thereof wherein

E represents CH or nitrogen;

Ar is phenyl, 2-, 3-, or 4-pyridyl, 2- or 3-thienyl, 4-or 5-pyrimidinyl, each of which is monosubstituted or optionally di- or trisubstituted with halogen, hydroxy, lower alkyl, or lower alkoxy, provided that at least one of the ortho positions of Ar is substituted;

$R_3$ and $R_4$ are not both hydrogen and independently represent hydrogen, lower alkyl, phenyl, 2-, 3-, 4-pyridyl, 2-or 3-thienyl or 2-, 4-, or 5-pyrimidinyl, each of which is optionally mono- or disubstituted with halogen, hydroxy, lower alkyl, or lower alkoxy;

phenylalkyl, 2-, 3-, or 4-pyridylalkyl, 2-or 3-thienylalkyl, or 2-, 4-, or 5-pyrimidinylalkyl, where each alkyl is lower alkyl, cycloalkyl having 3–8 carbon atoms, cycloalkyl lower alkyl, 2-hydroxyethyl or 3-hydroxypropyl, each of which is optionally mono or disubstituted with lower alkyl; and $R_5$ is lower alkyl.

* * * * *